United States Patent

Ozaki et al.

[11] 4,267,326
[45] May 12, 1981

[54] URACIL DERIVATIVES

[75] Inventors: Shoichiro Ozaki, Kamakura; Yoshimasa Ike, Yokohama; Katsutoshi Ishikawa, Yugawara; Haruki Mori, Yokohama, all of Japan

[73] Assignee: Mitsui Toatsu Chemicals, Incorporated, Tokyo, Japan

[21] Appl. No.: 15,149

[22] Filed: Feb. 26, 1979

Related U.S. Application Data

[63] Continuation-in-part of Ser. No. 829,914, Sep. 1, 1977, abandoned.

[30] Foreign Application Priority Data

Sep. 6, 1976 [JP] Japan .................................. 51-105714

[51] Int. Cl.³ .......................................... C07D 239/54
[52] U.S. Cl. ..................................... 544/313; 424/251
[58] Field of Search ......................................... 544/313

[56] References Cited

FOREIGN PATENT DOCUMENTS 51-98280 8/1976 Japan ....................................... 544/313

OTHER PUBLICATIONS

Ishikawa et al., Chemical Abstracts, vol. 86 (1977), 121,361c.

Primary Examiner—Paul M. Coughlan, Jr.
Attorney, Agent, or Firm—William J. Daniel

[57] ABSTRACT

New uracil derivatives of the general formula:

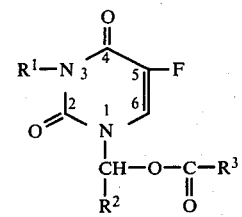

wherein $R^1$ stands for a hydrogen atom or a grouping of the formula:

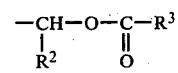

$R^2$ for a hydrogen atom, an alkyl group or a phenyl group and $R^3$ for an alkyl group or a phenyl group, with the proviso that when both $R^1$ and $R^2$ stand for a hydrogen atom, $R^3$ stands for a phenyl group or a straight chain alkyl group with 3~11 carbon atoms, that when $R^1$ stands for a hydrogen atom and $R^2$ for methyl group, $R^3$ stands for an alkyl group with at least 2 carbon atoms or a phenyl group, and that when $R^1$ stands for a hydrogen atom and $R^3$ for methyl group, $R^2$ stands for an alkyl group with at least 2 carbon atoms or a phenyl group. These uracil derivatives are prepared by reacting 5-fluorouracil with an α-haloalkyl carboxylate or with an aldehyde diacylate or by hydrolyzing a 1,3-bis-(acyloxymethyl)-5-fluorouracil with an acid or alkali. These uracil derivatives are useful as improved antitumor agents especially for oral administration and injection.

7 Claims, No Drawings

URACIL DERIVATIVES

This application is a continuation-in-part of application Ser. No. 829,914 filed on Sept. 1, 1977 by the same inventors and now abandoned.

BACKGROUND OF THE INVENTION

The present invention relates to new uracil derivatives and processes for preparing same. More particularly, the present invention relates to new 1-acyloxymethyl-5-fluorouracil derivatives and 1,3-bis(acyloxymethyl)-5-fluorouracil derivatives and processes for preparing same.

Heretofore, various kinds of uracil derivatives have been developed as anti-tumor agents. Concerning 1-acyloxymethyl-5-fluorouracil derivatives, however, no study have been made by any person other than the present inventors. More precisely, 1-acetoxymethyl-5-fluorouracil, 1-pivaloyloxymethyl-5-fluorouracil and 1-palmitoyloxymethyl-5-fluorouracil were developed for the first time by the present inventors as a new class of uracil derivatives and disclosed in Japanese Patent Prov. Publn. No. 98280/76.

However, the above mentioned 1-acyloxymethyl-5-fluorouracil derivatives are disadvantageous in that 1-acetoxymethyl-5-fluorouracil shows high toxicity, 1-pivaloyloxymethyl-5-fluorouracil weak anti-tumor activity and 1-palmitoyloxymethyl-5-fluorouracil poor absorbability in living body. Thus, there is still a great demand for developing new anti-tumor agents of 1-acyloxymethyl-5-fluorouracil series, which are strong in anti-tumor activity and possess good absorbability in living body with very low toxicity.

BRIEF SUMMARY OF THE INVENTION

Accordingly, it is an object of the present invention to provide new uracil derivatives which are effective anti-tumor agents, especially useful for injection and oral administration.

It is another object of the present invention to provide new uracil derivatives which are strong in anti-tumor activity and possess good absorbability in living body with very low toxicity.

It is still another object of the present invention to provide a process for the preparation of the new uracil derivatives.

It is further object of the present invention to provide the use of the uracil derivatives as anti-tumor agents for injection.

Other objects, features and advantages of the present invention will become apparent more fully from the following description.

DETAILED DESCRIPTION OF THE INVENTION

It has now been found that 1-acyloxymethyl-5-fluorouracil derivatives and 1,3-bis(acyloxymethyl)-5-fluorouracil derivatives which can be obtained by reacting 5-fluorouracil with an α-haloalkyl carboxylate or an aldehyde diacylate or by hydrolyzing a different kind of 1,3-bis(acyloxymethyl)-5-fluorouracil derivative with an acid or alkali exhibit a high level of anti-tumor activity and are particularly useful as anti-tumor agents for oral administration and injection.

In accordance with the present invention, there is provided a new uracil derivative of the general formula:

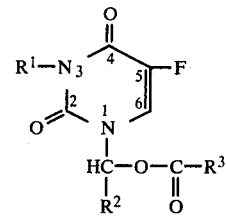

wherein $R^1$ stands for a hydrogen atom or a grouping of the formula:

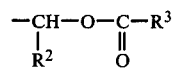

$R^2$ for a hydrogen atom, an alkyl group or a phenyl group and $R^3$ for an alkyl group or a phenyl group, with the proviso that when both $R^1$ and $R^2$ stand for a hydrogen atom, $R^3$ stands for a phenyl group or a straight chain alkyl group with 3~11 carbon atoms, that when $R^1$ stands for a hydrogen atom and $R^2$ for methyl group, $R^3$ stands for an alkyl group with at least 2 carbon atoms or a phenyl group, and that when $R^1$ stands for a hydrogen atom and $R^3$ for methyl group, $R^2$ stands for an alkyl group with at least 2 carbon atoms or a phenyl group.

When $R^1$ and $R^2$ each represent an alkyl group, they may be the same or different. Preferable examples of the alkyl group include a straight or branched chain alkyl group with 1~18 carbon atoms, such as methyl, ethyl, n-propyl, isopropyl, n-butyl, isobutyl, tert-butyl, n-pentyl, n-hexyl, n-heptyl, n-octyl, n-nonyl, n-decyl, undecyl, dodecyl, myristyl, heptadecyl or octadecyl group. The phenyl group may carry one or more substituents selected from alkyl groups, alkoxy groups and halogen atoms.

Illustrative of the typical uracil derivatives of the present invention are, for example, 1-butyryloxymethyl-5-fluorouracil, 1-valeryloxymethyl-5-fluorouracil, 1-caproyloxymethyl-5- fluorouracil, 1-enanthoyloxymethyl-5-fluorouracil, 1-lauroyloxymethyl-5-fluorouracil, 1-benzoyloxymethyl-5-fluorouracil, 1-(α-acetoxy-α-phenyl)methyl-5-fluorouracil, 1,3-bis(acetoxymethyl)-5-fluorouracil, 1,3-bis(palmitoyloxymethyl)-5-fluorouracil and 1,3-bis(pivaloyloxymethyl)-5-fluorouracil.

In accordance with the present invention, there is also provided a process for the preparation of the uracil derivatives. In one embodiment of the process, the uracil derivatives of the general formula:

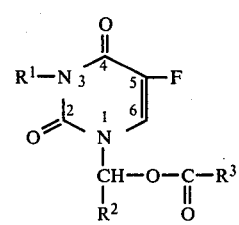

wherein $R^1$, $R^2$ and $R^3$ have the same meanings as given above, are prepared by reacting 5-fluorouracil with an α-haloalkyl carboxylate of the general formula:

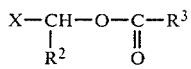

wherein $R^2$ and $R^3$ have the same meanings as given above and X stands for a halogen atom, preferably in the presence of an acid-binding agent and in a polar solvent which is inert to the reaction and capable of dissolving the starting 5-fluorouracil.

The α-haloalkyl carboxylate (or called acyloxymethyl halide) of the general formula [II] used as one of the reactants in the above process are known or can easily be prepared according to a method known per se. Preferable examples of the radical X are chlorine atom and bromine atom, with the chlorine atom being most preferable for economical reasons. Illustrative of the α-haloalkylcarboxylate are, for example, chloromethyl butyrate (or called butyryloxymethyl chloride), chloromethyl caproate, chloromethyl caprylate, chloromethyl laurate, chloromethyl myristate, α-chloroethyl caprylate, α-chloro-n-butyl acetate, chloromethyl benzoate and α-chlorobenzyl acetate. Chloromethyl propionate, chloromethyl palmitate and chloromethyl pivalate can also be used for the preparation of 1,3-bis(acyloxymethyl)-5-fluorouracil compounds.

No critical limitation exists in the proportion of the 5-fluorouracil to the α-haloalkyl carboxylate but these reactants are usually used in a stoichiometrical proportion. For example, when the product of the general formula [I] wherein $R^1$ stands for a hydrogen atom (i.e. 1-monosubstituted product) is to be prepared, usually, 5-fluorouracil may be reacted with an equimolar amount of the α-haloalkyl carboxylate. If 1,3-disubstituted product is to be prepared, however, 5-fluorouracil may be reacted with a doublemolar amount of the α-haloalkyl carboxylate to increase the yield of the product.

The above process is usually carried out in the presence of an acid-binding agent and a normally liquid polar solvent which is inert to the reaction but is capable of dissolving the starting materials. In general, 5-fluorouracil and the α-haloalkyl carboxylate are miscible with or easily soluble in such polar solvent. Examples of such polar solvent include N,N-dialkylcarboxyamides such as dimethylformamide and dimethylacetamide and dialkylsulfoxides such as dimethylsulfoxide. Acetonitrile can also be used as the solvent.

Examples of the acid-binding agent include inorganic bases such as alkali metal hydroxides, alkali metal hydrides, alkali metal carbonates and alkali metal bicarbonates; and organic bases such as aliphatic and aromatic tertiary amines and tetraalkylammonium hydroxides. The use of sodium hydride, potassium carbonate, triethylamine and pyridine is preferable. If the reactants are soluble in such aliphatic or aromatic tertiary amine, a part or all of the polar solvent may be replaced with such tertiary amine.

The reaction is carried out at a temperature within a range from 0° C. to 100° C., preferably from room temperature to 50° C. The reaction time depends on the reaction temperature adopted but is usually within a range of 1~20 hours, preferably 2~10 hours. In general, the reaction is carried out conveniently under normal atmospheric pressure.

After completion of the condensation reaction, the product aimed at is isolated and purified, for example, according to the following after-treatments. The reaction liquid is filtered to remove insoluble matters chiefly composed of an inorganic salt or a tertiary amine hydrohalide and then the solvent used is removed by distillation preferably under subatmospheric pressure. The distillation residue is subjected to a chromatographic treatment wherein a column packed with silica gel and a mixture of benzene-ethyl acetate as a developing solvent are used. By this chromatographic treatment, the crude end product is separated from 3-substituted isomer formed as by-product and unreacted starting materials. Alternatively, the distillation residue is taken up in chloroform and the chloroform solution is filtered to remove insoluble 5-fluorouracil, washed with water and dried. By removing chloroform by distillation, the crude end product is obtained. In certain cases, the reaction product may be poured into water whereby the inorganic salt or tertiary amine hydrohalide formed during the condensation reaction is dissolved in water and water-insoluble organic matters including the end product are precipitated. The crude end product thus obtained can be purified by recrystallization from benzene, ethanol or ether or by dissolving the crude product in chloroform and pouring the solution into a solvent in which the product is insoluble.

According to another embodiment of the process of the present invention, the uracil derivatives of the general formula:

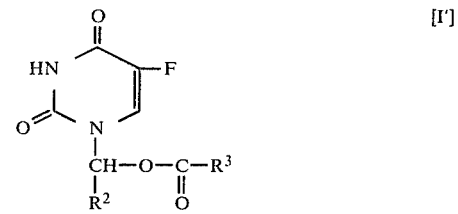

wherein $R^2$ and $R^3$ have the same meanings as give above, are prepared by hydrolyzing an N,N'-disubstituted uracil derivative of the general formula:

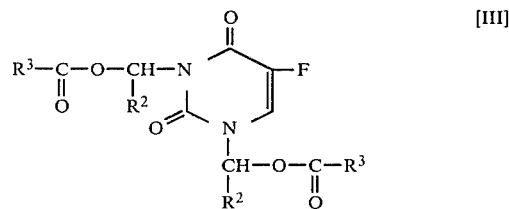

wherein $R^2$ and $R^3$ have the same meanings as given above, with a reagent selected from the group consisting of an acid and alkali.

A strong mineral acid such as hydrochloric acid or sulfuric acid as well as an aqueous solution thereof which may contain a water-miscible organic polar solvent comes into question as the acid for hydrolysis. A strong inorganic base such as caustic alkali can be used as the alkali for hydrolysis. The use of an aqueous solution of a caustic alkali such as an aqueous solution of sodium hydroxide which may contain a water-miscible organic solvent such as ethanol is especially preferable.

The hydrolyzing reaction is usually carried out by dissolving the starting N,N'-disubstituted compound of the general formula [III] in a solvent and adding slowly to the solution an acid or alkali or an aqueous solution thereof to keep the pH value of the liquid within the range of 10~11 and stirring the mixture until the hydrolyzing reaction is finished. This reaction is conducted usually at a temperature ranging from 0° C. to 100° C., preferably from room temperature to 80° C. for 1~8 hours, preferably 2~5 hours. The reaction mixture may be gently heated to accelerate the hydrolyzing reaction.

After completion of the hydrolyzing reaction, the reaction liquid is concentrated preferably under reduced pressure and allowed to cool whereby the crude product is precipitated out which is then collected by filtration. As the crude product contains impurities including side reaction products, e.g. 3-substituted isomer formed as by-product, the crude product is isolated and purified according to the aforementioned aftertreatments utilizing the column chromatographic treatment. This embodiment can be utilized for converting the N,N-disubstituted product formed as by-product in the firstly mentioned condensation reaction into the 1-monosubstituted end product.

According to still another embodiment of the process of the present invention, the uracil derivatives of the general formula:

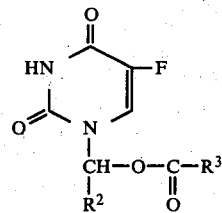

[I']

wherein $R^2$ and $R^3$ have the same meanings as given above, are prepared by reacting 5-fluorouracil with an aldehyde diacylate of the general formula:

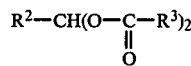

[IV]

wherein $R^2$ and $R^3$ have the same meanings as given above.

In this reaction, 2,4-bis(trimethylsilyl)-5-fluorouracil of the following structural formula:

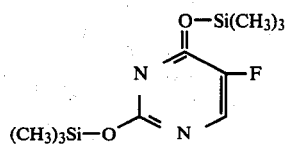

[V]

may be used in place of a part or all of the 5-fluorouracil.

The above reaciton is usually carried out in the presence of an acidic catalyst as reaction promoter. Examples of the acidic catalyst include various kinds of Lewis acid such as sulfuric acid, stannic chloride, titanium tetrachloride, ferric chloride, aluminum trichloride and the like. The aldehyde diacylates of the general formula [IV] are known compounds or can easily be prepared by a method known per se.

The reaction is conducted by dissolving 5-fluorouracil or 2,4-bis(trimethylsilyl) derivative thereof in a normally liquid organic solvent which is inert to the reaction, such as chloroform or carbon tetrachloride, and addig the acidic catalyst at a temperature ranging from $-10°$ C. to 100° C., preferably from 0° C. to 50° C. After completion of the reaction, the solvent is removed and the crude product is isolated and purified according to the aforesaid aftertreatments.

The new uracil derivatives of the present invention exhibit a high level of anti-tumor activity with a very slight side effect and are easily soluble in an injection medium. Thus, the uracil derivatives of this invention are valuable especially for use in oral administration and injection.

The present invention will now be illustrated in more detail by way of examples.

EXAMPLE 1

In a 300 cc 4-necked flask equipped with a stirrer, a thermometer and a dropping funnel were placed 80 ml of dimethylformamide. Then, 10.41 g (0.08 mol) of 5-fluorouracil was dissolved in the dimethylformamide and 24.29 g (0.24 mol) of triethylamine was added to this solution. To the mixture was added dropwise over 15 minutes 10.93 g (0.08 mol) of butyryloxymethyl chloride. The mixture was reacted together for 5 hours at room temperature and the reaction liquid was filtered to remove the precipitated triethylamine hydrochloride. The solvent was then distilled from the filtrate and the residue was subjected to a treatment using a column packed with silica gel and a mixture (1:1 in mixing ratio) of benzene and ethyl acetate whereby crude 1-butyryloxymethyl-5-fluorouracil was isolated. This crude product was recrystallized from benzene whereby 16.0 g of pure white crystals having a melting point of 96°~98° C. were obtained in a yield of 86.9%.

A result of elementary analysis of the product was well in agreement with the calculated value as follows:

| | Elementary analysis as $C_9H_{11}FN_2O_4$: | | | |
|---|---|---|---|---|
| | C | H | F | N |
| Found (%) | 47.12 | 4.73 | 8.08 | 12.82 |
| Calc. (%) | 46.96 | 4.82 | 8.25 | 12.17 |

A result of NMR absorption spectral analysis (solvent: DMSO-$d_6$) of this product was as follows:

$\delta = 0.92$ (3H, t, J=8, CH$_3$), 1.60 (2H, m, CH$_2$), 2.35 (2H, t, J=8, COCH$_2$), 5.64 (2H, s, OCH$_2$), 8.17 (1H, d, J=6, C$_6$-H) and 12.02 (1H, broad, NH).

In IR-absorption spectral analysis, this product exhibited characteristic absorption bands at 3410, 3290, 3080, 2970, 2920, 2830, 1740(s), 1665, 1472, 1420, 1380, 1350, 1320, 1268, 1250, 1195, 1180, 1145, 1115, 1095, 1040, 1000, 900, 880, 790, 770 and 725 cm$^{-1}$.

EXAMPLE 2

Using a reactor similar to that used in Example 1, 3.90 g (0.03 mol) of 5-fluorouracil was dissolved in 50 ml of dimethylformamide. Then, 3.0 g of triethylamine was added to this solution. To the mixture was added dropwise 4.73 g (0.0287 mol) of caproyloxymethyl chloride. The mixture was reacted for 3 hours at 50° C. After completion of the reaction, the reaction liquid was filtered to remove the precipitated triethylamine hydrochloride and then the dimethylformamide was removed by distillation from the filtrate. Next, 50 ml of chloroform was added to the residue and the mixture was stirred and filtered to remove insoluble unreacted 5-fluorouracil. The chloroform phase was washed with water and then dried. By removing the chloroform by distillation, 3.0 g of 1-caproyloxymethyl-5-fluorouracil was obtained as white crystals having a melting point of 95°~96° C. in a yield of 38.7%.

A result of elementary analysis of the crystals was well in agreement with the calculated value as follows:

|  |  | Elementary analysis as $C_{11}H_{15}FN_2O_4$: |  |  |  |
|---|---|---|---|---|---|
|  |  | C | H | F | N |
| Found | (%) | 50.42 | 5.63 | 7.17 | 10.42 |
| Calc. | (%) | 51.16 | 5.85 | 7.36 | 10.85 |

A result of NMR absorption spectral analysis (solvent: $CDCl_3$) of this product was as follows:

$\delta=0.90$ (3H, t, J=6, $CH_3$), 1.34 (4H, m, $-CH_2C-H_2-$), 1.62 (2H, m, $COCH_2CH_2-$), 2.40 (2H, t, J=6, $-COCH_2-$), 5.68 (2H, s, $N-CH_2-$), 7.62 (1H, d, J=6, $C_6$-H) and 9.85 (1H, broad, NH).

In IR-absorption spectral analysis, this product exhibited characteristic absorption bands at 3420, 3260, 3065, 2940, 2920, 2850, 1720, 1684, 1655, 1463, 1408, 1368, 1255, 1200, 1168, 1137, 1108, 972 and 780 cm$^{-1}$.

EXAMPLE 3

In a mixture of 10 ml of pyridine and 10 ml of water was dissolved 4 g (0.01 mol) of 1,3-bis(benzoyloxymethyl)-5-fluorouracil. A 5% aqueous caustic soda solution was slowly added dropwise to the solution under agitation while maintaining the pH value of the liquid at 10~11. The mixture was kept for 4 hours at 60° C. whereby alkaline hydrolysis of the starting 1,3-bis(benzoyloxymethyl)-5-fluorouracil was effected. After completion of the hydrolysis reaction, the reaction liquid was concentrated under reduced pressure and cooled. Any remaining unreacted 1,3-bis(benzoyloxymethyl)-5-fluorouracil was then precipitated out and filtered off and the filtrate was subjected to a column chromatographic treatment using a column packed with silica gel. Using a mixture (3:1 in mixing ratio) of benzene and ethyl acetate as eluent, 1-benzoyloxymethyl-5-fluorouracil aimed at was separated as a first elution component. 3-Benzoyloxymethyl-5-fluorouracil formed as by-product was also separated as a second elution component. The yields of 1-benzoyloxymethyl-5-fluorouracil and 3-benzoyloxymethyl-5-fluorouracil were 0.92 g (yield: 35%) and 0.65 g, respectively. After recrystallization from benzene of the crude product, the desired 1-benzoyloxymethyl-5-fluorouracil was obtained as white crystals melting at 179°~180° C.

A result of NMR absorption spectral analysis (solvent: DMSO-d$_6$) of 1-benzoyloxymethyl-5-fluorouracil was as follows:

$\delta=5.87$ (2H, s, $-CH_2-$), 7.4 8.1 (5H, m,

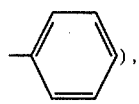

8.27 (1H, d, J=6, $C_6$-H) and 12.00 (1H, broad, NH).

In IR-absorption spectral analysis, the above compound exhibited characteristic absorption bands at 3410, 3385, 3365, 3255, 1730, 1720, 1700, 1659, 1597, 1463, 1449, 1408, 1372, 1272, 1260, 1242, 1200, 1165, 1144, 1106, 1091, 1068, 1041, 1023, 962, 778 and 702 cm$^{-1}$.

EXAMPLE 4

In 100 ml of dimethylacetamide were dissolved 19.51 g (0.15 mol) of 5-fluorouracil and 75.90 g (0.75 mol) of triethylamine. To this mixture was added dropwise at room temperature 41.05 g (0.165 mol) of chloromethyl laurate and the mixture was reacted together for 20 hours. After completion of the reaction, the triethylamine and dimethylacetamide were removed by distillation and the residue was poured into 400 ml of water. The mixture was stirred, filtered and washed with water whereby crystals were obtained which were then recrystallized from 200 ml of ethanol to obtain 38.06 g of 1-lauroyloxymethyl-5-fluorouracil having a melting point of 113.7~114.2° C. in a yield of 74.2%.

A result of elementary analysis of this product was well in agreement with the calculated value as follows:

|  |  | Elementary analysis as $C_{17}H_{27}Fn_2O_4$: |  |  |  |
|---|---|---|---|---|---|
|  |  | C | H | F | N |
| Found | (%) | 59.94 | 8.16 | 5.52 | 8.07 |
| Calc. | (%) | 59.63 | 7.95 | 5.55 | 8.19 |

A result of NMR absorption spectral analysis (solvent: $CDCl_3$) of this product was as follows:

$\delta=0.88$ (3H, t, J=8, $CH_3$), 1.24 (18H, m, $-(CH_2-)_9-$), 2.38 (2H, t, J=8, $COCH_2$), 5.63 (2H, s, $OCH_2$) and 7.63 (1H, d, J=6, $C_6$-H).

In IR-absorption spectral analysis, this product exhibited characteristic absorption bands at 3420, 3200, 3050, 2920(s), 2850, 1755, 1710(s), 1672, 1478, 1450, 1420, 1372, 1360, 1325, 1267, 1205, 1170, 1148(s), 1090, 1042, 1002, 995, 980, 972, 945, 790 and 720 cm$^{-1}$.

Table 1 shows results of synthetizing uracil derivatives of general formula [I'] in a similar manner to that described in Examples 1~3.

TABLE 1

| | | Uracil derivatives of the general formula [I'] | | | |
|---|---|---|---|---|---|
| Example No. | Yield (%) | Structural formula $R^2$ | $R^3$ | Melting point (°C.) | Positions in IR-region where main peak absorption bands are shown in IR-absorption spectral analysis (cm$^{-1}$) |
| 5 | 77.0 | H | $C_4H_9$ | 91~92 | 3420, 3070, 2940, 1740, 1720, 1468, 1362, 1260, 1140 and 785 |
| 6 | 82.8 | H | $C_6H_{13}$ | 109~110 | 3410, 2940, 1730(s), 1692, 1463, 1366 1254, 1140(s) and 780 |
| 7 | 73.6 | H | $C_7H_{15}$ | 112~113 | 3420, 2915, 1728(s), 1693, 1462, 1367, 1255, 1140(s) and 782 |
| 8 | 75.8 | H | $C_8H_{17}$ | 111~112 | 3030, 2923, 1730(s), 1695, 1468, 1372, 1260, 1142(s) and 785 |
| 9 | 68.0 | H | $C_9H_{19}$ | 115~116 | 3060, 2910, 1720, 1693(s), 1465, 1362, 1260, 1140(s) and 780 |
| 10 | 38.3 | $C_3H_7$ | $CH_3$ | 175~176 | 3160, 3040, 1744, 1726, 1695, 1655, 1462, 1373, 1205(s) and 775 |

TABLE 1-continued

Uracil derivatives of the general formula [I']

| Example No. | Yield (%) | Structural formula R² | R³ | Melting point (°C.) | Positions in IR-region where main peak absorption bands are shown in IR-absorption spectral analysis (cm⁻¹) |
| --- | --- | --- | --- | --- | --- |
| 11 | 57.0 | CH₃ | C₄H₉ | 132 | 3170, 3055, 1730(s), 1695, 1657, 1460, 1392, 1265(s), 1170 and 1088(s) |

EXAMPLE 12

In 70 ml of dimethylacetamide was dissolved 2.60 g (0.02 mol) of 5-fluorouracil. To this solution were added 0.96 g (0.02 mol) of 50% sodium hydride and then a solution of 2.16 g (0.02 mol) of chloromethyl acetate in 10 ml of dimethylacetamide. The mixture was reacted together at room temperature for 5.5 hours. After completion of the reaction, the reaction liquid was filtered to remove a precipitate and then the dimethylacetamide used as solvent was removed from the filtrate by distillation. The residue was taken up in 100 ml of ether and the ethereal solution was filtered to remove insoluble matters. The ether was removed by distillation and the residue was subjected to an adsorption treatment using a column packed with silica gel. The adsorbed substance was elutriated with a mixture (1:1 in mixing ratio) of benzene and ethyl acetate to isolate at first 180 mg of 1,3-bis(acetoxymethyl)-5-fluorouracil in a yield of 3.2%. This product was a viscous liquid and exhibited in IR-absorption spectral analysis characteristic absorption bands at 3120, 2970, 1755(s), 1704(s), 1690(s), 1478, 1375, 1285, 1230(s), 1170, 1087, 1035(s), 980, 842, 790 and 772 cm⁻¹.

EXAMPLE 13

Except that 6.10 g (0.02 mol) of chloromethyl palmitate was used in place of chloromethyl acetate used in Example 12, the operation of Example 4 was repeated whereby 1.02 g of 1,3-bis(palmitoyloxymethyl)-5-fluorouracil having a melting point of 80°∼80.5° C. was first obtained in a yield of 15.2%.

A result of elementary analysis of this product was well in agreement with the calculated value as follows:

| | | Elementary analysis as $C_{38}H_{67}FN_2O_6$: | | | |
| --- | --- | --- | --- | --- | --- |
| | | C | H | F | N |
| Found | (%) | 68.10 | 10.24 | 2.65 | 4.69 |
| Calc. | (%) | 68.43 | 10.13 | 2.85 | 4.20 |

A result of NMR absorption spectral analysis (solvent: CDCl₃) of this product was as follows:

δ=0.87 (6H, t, CH₃), 1.24 (52H, m, CH₂), 2.30 (4H, broad, —COCH₂), 5.71 (2H, s, CH₂O), 6.02 (2H, s, CH₂O) and 7.71 (1H, d, J=6, C₆-H).

In IR-absorption spectral analysis, this product exhibited characteristic absorption bands at 2900, 2830, 1740(s), 1690(s), 1467, 1355, 1280, 1162, 956, 864, 760 and 724 cm⁻¹.

EXAMPLE 14

In 40 ml of dimethylacetamide was dissolved 2.60 g (0.02 mol) of 5-fluorouracil. Then, 1.52 g (0.011 mol) of powdery potassium carbonate was added to this solution. To the mixture was added dropwise over one hour a solution of 3.31 g (0.022 mol) of chloromethyl pivalate in 10 ml of dimethylacetamide. The mixture was reacted together at room temperature for 15.5 hours. After completion of the reaction, the reaction liquid was filtered to remove a precipitate and then the dimethylacetamide used as solvent was removed from the filtrate by distillation. The residue was taken up in 30 ml of ether and after filtration for removing insoluble matters the ethereal filtrate was concentrated to obtain 2.52 g of crystals. The crystals were then recrystallized from ether whereby 1.88 g of 1,3-bis(pivaloyoxymethyl)-5-fluorouracil was obtained in a yield of 47.8% as white crystals having a melting point of 113°∼114° C.

A result of elementary analysis of this product was well in agreement with the calculated value as follows:

| | | Elementary analysis as $C_{16}H_{23}FN_2O_6$: | | | |
| --- | --- | --- | --- | --- | --- |
| | | C | H | F | N |
| Found | (%) | 54.02 | 6.69 | 4.99 | 7.72 |
| Calc. | (%) | 53.62 | 6.47 | 5.30 | 7.82 |

A result of NMR absorption spectral analysis (solvent: CCl₄) of this product was as follows:

δ=1.17 (9H, s, CH₃), 1.19 (9H, s, CH₃), 5.63 (2H, s, CH₂), 5.83 (2H, s, CH₂) and 7.70 (1H, d, J=6, C₆-H).

In IR-absorption spectral analysis, this product exhibited characteristic absorption bands at 3420, 2970, 1737(vs), 1685(s), 1482, 1470, 1450, 1366, 1268, 1130(vs), 1050, 1035, 980, 927, 888, 855, 800, 774 and 762 cm⁻¹.

EXAMPLE 15

In 100 ml of dimethylformamide was dissolved 7.80 g (0.06 mol) of 5-fluorouracil. Then, 10.24 g (0.06 mol) of chloromethyl benzoate was added to this solution. To this mixture was added dropwise slowly a solution of 6.07 g (0.06 mol) of triethylamine in 10 ml of dimethylformamide. The mixture was reacted together at room temperature for 6 hours. After completion of the reaction, the reaction liquid was filtered to remove the precipitated triethylamine hydrochloride and then the dimethylformamide used as solvent was removed from the filtrate by distillation. The residue was dissolved in 100 ml of chloroform and the solution was filtered to remove insoluble matters. The filtrate was washed and dried and then the chloroform was removed by distillation. The residue was subjected to a purifying treatment using a column packed with silica gel whereby 2.73 g of 1-benzoyloxymethyl-5-fluorouracil having a melting point of 178°∼180° C. and 8.43 g of 1,3-bis(benzoyloxymethyl)-5-fluorouracil as a viscous oily substance were isolated in yields of 17.1% and 35.4%, respectively.

A result of NMR absorption spectral analysis (solvent: DMSO-d₆ of 1-benzoyloxymethyl-5-fluorouracil was as follows:

δ=5.87 (2H, s, —CH₂—), 7.4∼8.1 (5H, m,

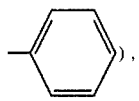, 8.27 (1H, d, J=6, C$_6$-H) and 12.00 (1H, broad, NH).

In IR-absorption spectral analysis, the above compound exhibited characteristic absorption bands at 3410, 3385, 3365, 3255, 1730, 1720, 1700, 1659, 1597, 1463, 1449, 1408, 1372, 1272, 1260, 1242, 1200, 1165, 1144, 1106, 1091, 1068, 1041, 1023, 962, 778 and 702 cm$^{-1}$.

On the other hand, a result of NMR absorption spectral analysis (solvent: DMSO-d$_6$) of 1,3-bis(benzoyloxymethyl)-5-fluorouracil was as follows:

δ=5.5 6.4 (4H, m, —CH$_2$—) and 7.4 8.2 (11H, m,

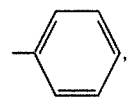,

—CH—)

In IR-absorption spectral analysis, the above compound exhibited characteristic absorption bands at 3110, 3078, 3000, 1768, 1755, 1743, 1707, 1608, 1591, 1462, 1381, 1329, 1270, 1190, 1169, 1100, 1073, 1055, 1032, 984, 770, 714 and 692 cm$^{-1}$.

EXAMPLE 16

In 20 ml of chloroform were dissolved 2.74 g (0.01 mol) of 2,4-bis(trimethylsilyl)-5-fluorouracil and 2.71 g (0.013 mol) of benzal diacetate. To this mixture was added dropwise slowly a solution of 2.0 g of stannic chloride in 10 ml of chloroform. After addition of the solution, the chloroform was removed by distillation and the residue was extracted with water. The extraction residue was dissolved in chloroform and decolored and thereafter the chloroform was distilled off. The residue was again dissolved in a small amount of chloroform and petroleum ether was added to the solution whereby a precipitate was formed which was then collected by filtration. In this manner, 1.06 g of 1-(α-acetoxy-α-phenyl)methyl-5-fluorouracil having a melting point of 172°~176° C. was obtained.

A result of NMR absorption spectral analysis (solvent: DMSO-d$_6$) of this product was as follows:

δ=2.22 (3H, s, CH$_3$), 7.53 (5H, s,

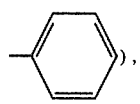, 7.82 (1H, s, CH), 7.91 (1H, α, J=6, C$_6$-H) and 12.2 (1H, broad, NH).

In IR-absorption spectral analysis, this product exhibited characteristic absorption bands at 3200, 3075, 2830, 1765, 1732, 1700(s), 1657, 1467, 1378, 1250, 1200, 1108, 1020, 980, 897, 782, 720 and 690 cm$^{-1}$.

The uracil derivatives of the present invention were examined according to the procedure set forth hereunder to determine their anti-tumor activities in terms of Percent Increase in Life Span (ILS %) which is now widely adopted as index to evaluation of antitumor activity. A result of the examination is shown in Table 2.

[Procedure for the Measurement of Anti-tumor Activity]

(1) L-1210:

Using a group consisting of six BDF$_1$ mice, 1×10$^5$ tumor cells of the lymphatic leukemia L-1210 (form the National Cancer Institute strain) were inoculated intraperitoneally to the individual mice. After the lapse of 24 hours from the inoculation of the tumor cells, the six mice thus inoculated were forced to receive, once a day, intraperitoneal injection (ip) or oral administration (po) of a given amount of a suspension of each test compound in 0.5% CMC for 5 days and survival days of the mice treated were recorded. ILS % was calculated according to the following equation in relation with the survival days of a control group of the mice.

$$ILS\ \% = \frac{T-C}{C} \times 100$$

wherein
T: days from the first day of administrating the test compound to the day when the treated group of mice die
C: days from the first day of administrating placebo to the day when the control group of mice die.

(2) S-180A:

Using a group consisting of six ddN mice, 1×10$^7$ tumor cells of sarcoma 180-A were inoculated intraperitoneally to the individual mice. After the lapse of 24 hours from the inoculation of the tumor cells, the six mice thus inoculated were forced to receive, once a day, intraperitoneal injection of a given amount of a suspension of each test compound in 0.5% CMC for 5 days. After the lapse of 7 days from the injection of the tumor cells, ascites were taken out to measure TPCV (total packed cell volume) which can be obtained according to the following equation:

$$TPCV = \frac{\text{tumor cell volume}}{\text{ascites volume}}$$

Also, TGR (tumor growth ratio) is calculated according to the following formula:

$$TGR = \frac{T}{C} \times 100$$

wherein
T: TPCV when a test compound was injected, and
C: TPCV when no test compound was injected.

It is evident from Table 2 that the uracil derivatives of the present invention exhibit high levels of anti-tumor activity and thus are suitable as anti-tumor agents.

TABLE 2

| Comp. No. | Test Compound Substituent | | | Tumor | | | | |
|---|---|---|---|---|---|---|---|---|
| | | | | L-1210 | | | S-180A | |
| | | | | ILS (%) | | Antitumor activity | TGR (%) | Antitumor activity |
| | $R^1$ | $R^2$ | $R^3$ | 30 mg/kg | 100 mg/kg | | 30 mg/kg | |
| 1 | H | H | $C_3H_7$ | 44 | 16 | +++ | 0 | +++ |
| 2 | H | H | $C_4H_9$ | 54 | 40 | +++ | 5.2 | +++ |
| 3 | H | H | $C_5H_{11}$ | 40 | 46 | +++ | 0 | +++ |
| 4 | H | H | $C_6H_{13}$ | 30 | 57 | +++ | 0 | +++ |
| 5 | H | H | $C_7H_{15}$ | 25 | 62 | +++ | 0 | +++ |
| 6 | H | H | $C_8H_{17}$ | 25 | 68 | +++ | 0 | +++ |
| 7 | H | H | $C_9H_{19}$ | 46 | 75 | +++ | 0 | +++ |
| 8 | H | H | $C_{11}H_{23}$ | 64 | 106 | +++ | 0 | +++ |
| 9 | H | H | $C_6H_5$ ($\phi$)* | 25 | 60 | +++ | 8 | +++ |
| 10 | H | $C_3H_7$ | $CH_3$ | 31 | 41 | +++ | 10 | +++ |
| 11 | H | $CH_3$ | $C_4H_9$ | 35 | 50 | +++ | 0 | +++ |
| 12 | H | $C_6H_5$ ($\phi$)* | $CH_3$ | 40 | 40 | +++ | 0 | +++ |
| 13 | $CH_2OOCC_4H_9$ | H | $C_4H_9$ | 30 | 32 | +++ | 5 | +++ |
| 14 | $CH_2OOC$-tert-$C_4H_9$ | H | tert-$C_4H_9$ | 35 | 40 | +++ | 8 | +++ |
| 15 | $CH_2OOCC_6H_{13}$ | H | $C_6H_{13}$ | 41 | 45 | +++ | 10 | +++ |
| 16 | $CH_2OOCC_7H_{15}$ | H | $C_7H_{15}$ | 45 | 69 | +++ | 10 | +++ |
| Known compounds | | | | | | | | |
| 17 | H | H | $CH_3$ | 41 | 6 | +++ | 85.3 | — |
| 18 | H | H | $C_2H_5$ | 44 | −2 | +++ | 18 | ++ |
| 19 | H | H | tert-$C_4H_9$ | 6 | 0 | − | 25.2 | ++ |
| 20 | H | H | $C_{15}H_{31}$ | 12 | 5 | + | 25 | ++ |

*The symbol "$\phi$" stands for phenyl group. (Alkyl substituents are straight chain one unless otherwise indicated.)

Notes:
(1) In the case of L-1210, the anti-tumor activity is indicated by the following symbolized ratings:
  − ILS (%) 0 ∼ 9
  + ILS (%) 10 ∼ 19
  ++ ILS (%) 20∼29
  +++ ILS (%) ≧30.
(2) In the case of S-180A, the anti-tumor activity is indicated by the following symbolized ratings:
  − TGR (%) 100 ∼ 66
  + TGR (%) 65 ∼ 41
  ++ TGR (%) 40 ∼ 11
  +++ TGR (%) 10 ∼ 0.

As is evident from the above table, the known compound No. 17 wherein $R^3$ is methyl group (having one carbon atom) exhibits high anti-tumor activity at a dose of 30 mg/kg but shows strong toxicity at a dose of 100 mg/kg. This compound scarcely shows anti-tumor activity to S-180A. The known compounds Nos. 19 and 20 exhibit poor anti-tumor activity to both L-1210 and S-180A. The known compound No. 18 displays high anti-tumor activity against L-1210 but its anti-tumor activity to S-180A is practically inferior.

In contrast, the compounds Nos. 1∼16 of the present invention exhibit high anti-tumor activity of the rating +++ against both L-1210 and S-180A. The anti-tumor activity to L-1210 becomes more remarkable as the number of carbon atoms in the straight chain alkyl group ($R^3$) increases from 3 to 11. Especially, it is surprising that the compound No. 8 shows an ILS value as high as 106 at a dose of 100 mg/kg. In the case of the compound No. 20 wherein the number of carbon atoms in $R^3$ is 15, the activity rather decreases significantly. The result reveals that the compounds having as $R^3$ a straight chain alkyl group with 3∼11 carbon atoms are excellent in anti-tumor activity as compared with the similar known compounds. The compound having —$C_3H_7$ (compound No. 10) or —$C_6H_5$ (compound No. 12) as $R^2$ exhibit high anti-tumor activity to both L-1210 and S-180A although these compounds have methyl group as $R^3$ as in the case of the know compound No. 17. This fact is indeed unexpected in view of similarity in structure. All of the 5-fluorouracil compounds having substituents in both 1- and 3-positions exhibit remarkable anti-tumor activity to both L-1210 and S-180A.

[Comparative Test]

A test compound was intraperitoneally injected (ip) to each rat of a group consisting of 6 rats at a rate of 50 mg/kg body weight and the change in concentration of the test compound in blood with the lapse of time was examined. A result of the test is shown in Table 3 below.

TABLE 3

| Test Compound Substituent | | | Concentration in blood Lapse of time after injection (Hours) | | | | Remarks |
|---|---|---|---|---|---|---|---|
| $R^1$ | $R^2$ | $R^3$ | 1 | 2 | 3 | 5 | |
| *H | H | $CH_3$ | 8.4 | 1.4 | N.D. | N.D. | (3 rats out of 5 rats dead) |
| *H | H | $C_2H_5$ | 6.8 | 4.2 | 1.2 | N.D. | |
| H | H | n-$C_3H_7$ | 5.7 | 3.3 | 0.8 | 0.02 | |
| H | H | n-$C_5H_{11}$ | 7.7 | 7.8 | 4.1 | 1.3 | |
| H | H | n-$C_{11}H_{23}$ | 4.3 | 6.5 | 0.9 | 0.05 | |
| *H | H | n-$C_{15}H_{31}$ | 1.2 | 1.8 | 0.2 | 0.01 | |
| H | H | phenyl | 3.7 | 2.8 | 0.4 | 0.02 | |
| H | phenyl | $CH_3$ | 6.1 | 1.3 | 0.1 | N.D. | |

Notes:
(1) The compounds with asterisk (*) are known compounds.
(2) The symbol "N.D." is an abbreviation of "not detected".

The above table reveals that 1-acetoxymethyl-5-fluorouracil as s similar known compound exhibits strong toxicity and rapid depression in the concentration in blood, that 1-palmitoyloxymethyl-5-fluorouracil as another similar known compound exhibits a lower concentration in blood and poor absorption in living body, and that 1-propionyloxymethyl-5-fluorouracil as the other known compound shows a high concentration comparable with the products of the present invention but is inferior in anti-tumor activity to S-180A as shown in Table 2. Contrary to this, the uracil derivatives of the present invention exhibit low toxicity and good absorption in living body in addition to high anti-tumor activity. It is in fact surprising that in spite of some similarity in structure to the known compounds, the uracil derivatives of the present invention are markedly distinguished by a combination of their low toxicity, strong anti-tumor activity and good absorbability in living body and high concentration in blood from the known compounds.

It is understood that the preceding representative examples may be varied within the scope of the present invention, both as to reactants and reaction conditions, by one skilled in the art to achieve essentially the same results.

As many widely different embodiments of this invention may be made without departing from the spirit and scope thereof, it is to be understood that this invention is not limited to the specific embodiments thereof except as defined in the appended claims.

What is claimed is:

1. Uracil derivatives of the general formula:

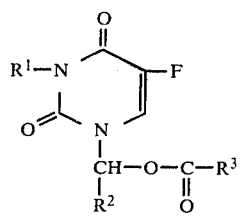

wherein:
  $R^1$ stands for a hydrogen atom;
  $R^2$ is a hydrogen atom and $R^3$ is phenyl or straight chain alkyl with 5–11 carbon atoms; or
  $R^2$ is n-propyl and $R^3$ is methyl; or
  $R^2$ is methyl and $R^3$ is n-butyl; or
  $R^2$ is phenyl and $R^3$ is methyl.
2. 1-Caproyloxymethyl-5-fluorouracil.
3. 1-Enanthoyloxymethyl-5-fluorouracil.
4. 1-Capryloxymethyl-5-fluorouracil.
5. 1-Lauroyloxymethyl-5-fluorouracil.
6. 1-Benzoyloxymethyl-5-fluorouracil.
7. 1-(α-acetoxy-α-phenyl)methyl-5-fluorouracil.

* * * * *